United States Patent
Binner et al.

(10) Patent No.: US 10,661,302 B2
(45) Date of Patent: *May 26, 2020

(54) PROCESS FOR FORMING A SHAPED FILM PRODUCT

(71) Applicant: Johnson & Johnson Consumer Inc., Skillman, NJ (US)

(72) Inventors: Curt Binner, Furlong, PA (US); Kenneth A. Pelley, Hopewell, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/581,010

(22) Filed: Dec. 23, 2014

(65) Prior Publication Data

US 2015/0182993 A1 Jul. 2, 2015

Related U.S. Application Data

(60) Provisional application No. 61/922,306, filed on Dec. 31, 2013.

(51) Int. Cl.
*B05D 1/32* (2006.01)
*B05D 1/36* (2006.01)
*A61K 9/70* (2006.01)

(52) U.S. Cl.
CPC ............ *B05D 1/322* (2013.01); *A61K 9/7007* (2013.01); *B05D 1/36* (2013.01); *Y10T 428/24802* (2015.01)

(58) Field of Classification Search
CPC ...................................................... B05D 1/322
See application file for complete search history.

(56) References Cited

U.S. PATENT DOCUMENTS 2,122,451 A * 7/1938 Cassimatis .............. C11C 5/008
264/132
2,267,787 A * 12/1941 Ciavola ................. B44C 1/1756
101/129

(Continued)

FOREIGN PATENT DOCUMENTS

CA 2250025 C 10/2006
CN 1148535 A 4/1997

(Continued)

OTHER PUBLICATIONS

International Search Report dated Apr. 30, 2015, International Application No. PCT/US2014/072107.

(Continued)

*Primary Examiner* — Nathan H Empie

(57) ABSTRACT

A process capable of commercial scale manufacturing of inexpensive, shaped film products includes placing a mask over a substrate; delivering a film-forming composition through a nozzle to form a raw shape on the substrate; removing the mask; and solidifying the film-forming composition to provide the shaped film product disposed on the substrate. The mask has a delivery surface and an opposite substrate-facing surface and at least one aperture having a design corresponding to the desired shaped film product. The nozzle is disposed in sealing engagement with the delivery surface of the mask to the at least one aperture of the mask during delivery of the film-forming composition.

8 Claims, 8 Drawing Sheets

(56) References Cited

U.S. PATENT DOCUMENTS

| | | | |
|---|---|---|---|
| 2,511,511 A * | 6/1950 | Murphy | B41F 15/0836 |
| | | | 101/120 |
| 2,523,670 A | 9/1950 | Shueler | |
| 2,852,252 A | 9/1958 | Sperry | |
| 3,198,109 A | 8/1965 | Dwyer et al. | |
| 3,421,455 A * | 1/1969 | Werner | A23G 3/02 |
| | | | 101/116 |
| 3,476,045 A | 11/1969 | Lusher | |
| 3,994,220 A * | 11/1976 | Vertegaal | B41F 31/08 |
| | | | 101/119 |
| 4,050,409 A | 9/1977 | Duchenaud et al. | |
| 4,068,994 A | 1/1978 | Cadwallader et al. | |
| 4,219,596 A * | 8/1980 | Takemoto | B31D 1/021 |
| | | | 156/231 |
| 4,379,185 A * | 4/1983 | Smith | B05C 1/10 |
| | | | 101/115 |
| 4,391,853 A * | 7/1983 | Pointon | B44C 1/1733 |
| | | | 156/231 |
| 4,466,431 A | 8/1984 | Tharrat et al. | |
| 4,604,966 A * | 8/1986 | Kohn | H05K 3/1233 |
| | | | 101/120 |
| 4,699,792 A | 10/1987 | Asmussen et al. | |
| 4,930,413 A | 6/1990 | Jaffa | |
| 4,990,339 A | 2/1991 | Scholl et al. | |
| 5,251,566 A | 10/1993 | Kobayashi et al. | |
| 5,264,269 A | 11/1993 | Kakiuchi et al. | |
| 5,393,529 A | 2/1995 | Hoffmann et al. | |
| 5,474,802 A | 12/1995 | Shimoda et al. | |
| 5,553,536 A | 9/1996 | Van Os | |
| 5,553,539 A | 9/1996 | Hasegawa | |
| 5,572,928 A | 11/1996 | Negishi | |
| 5,578,151 A | 11/1996 | Andris et al. | |
| 5,622,108 A | 4/1997 | Benedetto et al. | |
| 5,700,478 A | 12/1997 | Biegajski et al. | |
| 5,746,127 A | 5/1998 | Fischbeck et al. | |
| 5,780,142 A * | 7/1998 | Kume | B44C 1/165 |
| | | | 428/195.1 |
| 5,780,418 A | 7/1998 | Niinaka et al. | |
| 5,800,832 A | 9/1998 | Tapolsky et al. | |
| 5,814,260 A | 9/1998 | Arai | |
| 5,914,118 A | 6/1999 | Yamamura et al. | |
| 5,925,414 A | 7/1999 | Buechele et al. | |
| 5,948,430 A | 9/1999 | Zerbe et al. | |
| 6,092,464 A | 7/2000 | Meola et al. | |
| 6,132,510 A | 10/2000 | Buechele et al. | |
| 6,159,498 A | 12/2000 | Tapolsky et al. | |
| 6,199,479 B1 | 3/2001 | Isozaki et al. | |
| 6,238,741 B1 | 5/2001 | Blazick et al. | |
| 6,395,087 B1 * | 5/2002 | Jairazbhoy | B23K 3/0607 |
| | | | 118/406 |
| 6,429,261 B1 | 8/2002 | Lang et al. | |
| 6,444,214 B1 | 9/2002 | Cole et al. | |
| 6,495,080 B1 | 12/2002 | Tsai et al. | |
| 6,537,663 B1 | 3/2003 | Chang et al. | |
| 6,548,592 B1 | 4/2003 | Lang et al. | |
| 6,565,839 B2 | 5/2003 | de la Poterie et al. | |
| 6,576,575 B1 | 6/2003 | Griesbach, III et al. | |
| 6,592,887 B2 | 7/2003 | Zerbe et al. | |
| 6,595,129 B2 | 7/2003 | Mori | |
| 6,656,274 B2 | 12/2003 | Claassen et al. | |
| 6,659,004 B2 | 12/2003 | Tagami | |
| 6,722,275 B2 | 4/2004 | Coleman et al. | |
| 6,800,295 B2 | 10/2004 | Fox | |
| 6,946,501 B2 | 9/2005 | Kochvar et al. | |
| 6,989,327 B2 | 1/2006 | Sharma et al. | |
| 7,285,520 B2 | 10/2007 | Krzysik et al. | |
| 7,332,230 B1 | 2/2008 | Krumme | |
| 7,378,360 B2 | 5/2008 | Clark et al. | |
| 7,387,787 B2 | 6/2008 | Fox | |
| 7,579,019 B2 | 8/2009 | Tapolsky et al. | |
| 7,612,048 B2 | 11/2009 | Pinna et al. | |
| 7,803,430 B2 | 9/2010 | Krumme | |
| 8,042,463 B2 | 10/2011 | Sato | |
| 8,268,764 B2 | 9/2012 | Glenn, Jr. et al. | |
| 8,349,341 B2 | 1/2013 | Glenn, Jr. et al. | |
| 8,349,786 B2 | 1/2013 | Glenn, Jr. et al. | |
| 8,349,787 B2 | 1/2013 | Glenn, Jr. et al. | |
| 8,354,393 B2 | 1/2013 | Maruyama | |
| 8,415,287 B2 | 4/2013 | Glenn, Jr. et al. | |
| 8,741,194 B1 | 6/2014 | Ederer et al. | |
| 2001/0004152 A1 | 6/2001 | Treleaven et al. | |
| 2002/0068251 A1 * | 6/2002 | Steck | B44C 1/17 |
| | | | 431/288 |
| 2002/0098994 A1 | 7/2002 | Zafar | |
| 2002/0127254 A1 | 9/2002 | Fotinos et al. | |
| 2002/0160062 A1 | 10/2002 | Liu et al. | |
| 2002/0192287 A1 | 12/2002 | Mooney et al. | |
| 2003/0175333 A1 | 9/2003 | Shefer et al. | |
| 2003/0209485 A1 | 11/2003 | Kools | |
| 2003/0211115 A1 | 11/2003 | Kulkarni et al. | |
| 2003/0235606 A1 | 12/2003 | Nussen | |
| 2003/0235630 A1 | 12/2003 | Nussen | |
| 2004/0180077 A1 | 9/2004 | Riker | |
| 2005/0145832 A1 | 7/2005 | Wessling et al. | |
| 2005/0208110 A1 | 9/2005 | Singh et al. | |
| 2006/0002987 A1 | 1/2006 | Bevacqua et al. | |
| 2007/0298087 A1 | 12/2007 | Biegajski | |
| 2008/0057087 A1 | 3/2008 | Krumme | |
| 2008/0102103 A1 | 5/2008 | Bevacqua et al. | |
| 2008/0282914 A1 | 11/2008 | Black et al. | |
| 2010/0053577 A1 | 3/2010 | Lee | |
| 2012/0094004 A1 | 4/2012 | Stopek et al. | |
| 2012/0100202 A1 | 4/2012 | Bogue | |
| 2012/0141698 A1 | 6/2012 | Oleary et al. | |
| 2012/0201964 A1 | 8/2012 | Zhou et al. | |
| 2013/0092721 A1 * | 4/2013 | Trelford | H05K 3/4069 |
| | | | 228/256 |
| 2015/0182990 A1 | 7/2015 | Binner et al. | |
| 2015/0182991 A1 | 7/2015 | Binner et al. | |
| 2015/0182992 A1 | 7/2015 | Binner et al. | |
| 2017/0354990 A1 | 12/2017 | Binner et al. | |
| 2017/0368568 A1 | 12/2017 | Binner et al. | |
| 2019/0217333 A1 | 7/2019 | Binner et al. | |

FOREIGN PATENT DOCUMENTS

| | | |
|---|---|---|
| CN | 201240095 Y | 5/2009 |
| CN | 103476565 A | 12/2013 |
| DE | 3423328 A1 | 1/1986 |
| EP | 781546 A | 7/1997 |
| EP | 1110541 A1 | 6/2001 |
| EP | 1149572 A1 | 10/2001 |
| EP | 2472331 A1 | 7/2012 |
| FR | 2710869 A1 | 4/1995 |
| JP | A-S49-135714 | 11/1976 |
| JP | S57170732 A | 10/1982 |
| JP | 63171565 A | 7/1988 |
| JP | H10156849 A | 6/1998 |
| JP | 2003126761 A | 5/2003 |
| JP | 2013/540161 | 4/2012 |
| JP | 201286015 | 5/2012 |
| JP | 2012186015 | 9/2012 |
| JP | 2013/188872 | 9/2013 |
| JP | 2015086015 A | 5/2015 |
| WO | WO1998/017251 A | 4/1998 |
| WO | WO2001/034121 A | 5/2001 |
| WO | WO2005/009386 A | 2/2005 |
| WO | WO 2009/084234 A | 7/2009 |
| WO | WO2012/104834 A | 8/2012 |
| WO | WO 2014/116770 A | 7/2014 |

OTHER PUBLICATIONS

U.S. Appl. No. 14/580,974, filed Dec. 23, 2014, Binner et al.
U.S. Appl. No. 61/922,287, filed Dec. 31, 2013, Binner et al.
U.S. Appl. No. 14/580,977, filed Dec. 23, 2014, Binner et al.
U.S. Appl. No. 61/922,296, filed Dec. 31, 2013, Binner et al.
U.S. Appl. No. 61/922,306, filed Dec. 31, 2013, Binner et al.
U.S. Appl. No. 14/581,057, filed Dec. 23, 2014, Binner et al.
U.S. Appl. No. 61/922,318, filed Dec. 31, 2013, Binner et al.
Kapur et al., "Predicting the Behavior of Screen Printing", IEEE

(56) References Cited

OTHER PUBLICATIONS

Transactions on Components, Packaging and Manufacturing Technology, vol. 3, No. 3 (Mar. 2013), pp. 508-515.
Willfahrt et al., "Optimising Stencil Thickness and Ink Film Deposit", (2011), International Circular of Graphic Education and Research.
U.S. Appl. No. 14/580,974, filed Dec. 23, 2014, 2015-0182991, Jul. 2, 2015, Abandoned.
U.S. Appl. No. 61/922,287, filed Dec. 31, 2013, Expired.
U.S. Appl. No. 16/366,533, filed Mar. 27, 2019, 2019-0217333, Jul. 18, 2019, Pending.
U.S. Appl. No. 14/580,977, filed Dec. 23, 2014, 2015-0182992, Jul. 2, 2015, Abandoned.
U.S. Appl. No. 61/922,296, filed Dec. 31, 2013, Expired.
U.S. Appl. No. 16/584,146, filed Sep. 26, 2019, Pending.
U.S. Appl. No. 14/581,010, filed Dec. 23, 2014, 2015-0182993, Jul. 2, 2015, Pending.
U.S. Appl. No. 61/922,306, filed Dec. 31, 2013, Expired.
U.S. Appl. No. 15/688,217, filed Aug. 28, 2017, 2017-0368568, Dec. 28, 2017, Abandoned.
U.S. Appl. No. 15/688,411, filed Aug. 28, 2017, 2017-0354990, Dec. 14, 2017, U.S. Pat. No. 10,016,784, Jul. 10, 2018, Grant.
U.S. Appl. No. 14/581,057, filed Dec. 23, 2014, 2015-0182990, Jul. 2, 2015, U.S. Pat. No. 9,839,939, Dec. 12, 2017, Grant.
U.S. Appl. No. 61/922,318, filed Dec. 31, 2013, Expired.
Ebara, "Techniques of Wallpaper manufactured by Rotary Screen Printing", Journal of Printing Science and Technology, Japan, 2001, 38(1):13-17.
Chang et al., "Pharmaceutics", China Medical Science and Technology Press, 2008, pp. 265-266.

\* cited by examiner

PROCESS FOR FORMING A SHAPED FILM PRODUCT

This application claims the benefit of U.S. provisional 61/922,306 filed on Dec. 31, 2013, the complete disclosure of which is hereby incorporated herein by reference for all purposes.

BACKGROUND

Film products have a wide variety of uses. These include decorative window decals, plasters, adhesive bandages, and oral strips (both medicated and otherwise).

Conventional production of such integral film products generally involves die-cutting the desired shaped product from film stock. While this production produces inexpensive film stock, die-cutting limits the efficiency and/or variability of final product forming. If the product shape is not completely rectangular or otherwise completely tessellated, the surrounding ladder scrap can produce significant waste. Therefore, products that have costly raw materials are often restricted to square or other completely tessellated shapes to substantially eliminate this expensive waste. This unfortunately prevents the formation of optimal shapes for some uses. Examples of die-cutting medical films include such production techniques are described in Pharmedica Ltd., WO 2012104834 A1, Pinna et al, U.S. Pat. No. 7,612,048 B2, and Smithkline Beecham Corp., WO 2005/009386 A2.

On the other hand, printing—including stencil printing and screen printing—are known processes that are capable of providing irregular shapes on substrates. Generally, the printed materials remain on permanently joined to the substrates, such as printed text and graphics on paper, printed circuits in the electronics industry, and printed designs on clothing and signage. However, such integration of a carrying substrate into a printed element prevents the usage of the printed product separate from the substrate.

What is needed is a process capable of commercial scale manufacturing of inexpensive, film products without the waste of die-cutting and which products are capable of use independent of a supporting structure on which they are formed.

SUMMARY

Surprisingly, we have found a process capable of commercial scale manufacturing of inexpensive, shaped film products without the waste of die-cutting. The process includes placing a mask over a substrate; delivering a film-forming composition through a nozzle to form a raw shape on the substrate; removing the mask; and solidifying the film-forming composition to provide the shaped film product disposed on the substrate. The mask has a delivery surface and an opposite substrate-facing surface and at least one aperture having a design corresponding to the desired shaped film product. The nozzle is disposed in sealing engagement with the delivery surface of the mask to the at least one aperture of the mask during delivery of the film-forming composition.

In an alternative embodiment, a process includes placing a first mask over a substrate; delivering a first film-forming composition through a nozzle to form a first raw shape on the substrate; removing the first mask; placing a second mask over the first raw shape; controlling delivery of a second film-forming composition to a void volume defined by a projection of a delivery opening of a nozzle, substrate and mask sidewalls and delivering the controlled volume of the second film-forming composition to the second mask aperture; removing the second mask; and solidifying the first and second raw shapes to provide the shaped film product disposed on the substrate. The first mask has a delivery surface and an opposite substrate-facing surface and at least one aperture having a design corresponding to a desired shape of a first layer of the shaped film product, and the nozzle is placed in contact with the delivery surface through the at least one aperture of the mask. The second mask has a delivery surface and an opposite substrate-facing surface and at least one aperture having a design corresponding to the desired shape of a second layer of the shaped film product.

DETAILED DESCRIPTION OF THE PREFERRED EMBODIMENTS

The present invention relates to a process and apparatus for forming shaped film products. The following description is presented to enable one of ordinary skill in the art to make and use the invention. Various modifications to the embodiments and the generic principles and features described herein will be readily apparent to those skilled in the art. Thus, the present invention is not intended to be limited to the embodiments shown but is to be accorded the widest scope consistent with the principles and features described herein. Shaped film products may have a wide variety of uses. These include household and recreational uses, such as decorative decals for windows and walls, temporary tattoos (such as body decals), healthcare devices such as medicated and/or absorbent plasters, adhesive bandages and other wound coverings, oral strips also known as a "consumable film" (medicated, therapeutic, and cosmetic), other body strips, such as moisturizing, acne treatment, lightening of dark circles, melisma, cellulite, delivery of vitamins, treatment of eczema, psoriasis, and the like.

As used herein the specification and the claims, the term "integral film product" variants thereof relate to a film product that is sufficiently robust to permit handling for a desired purpose separate from any supporting substrate. The product is removable from a substrate for use independent of the substrate.

As used herein the specification and the claims, the term "film-forming composition" variants thereof relate to a composition that is capable of forming, by itself or in the presence of an additional agent, a continuous film on a substrate.

As used herein the specification and the claims, the term "raw shape" variants thereof relate to the shaped volume of film-forming composition disposed on a substrate through an apertured mask. The raw shape generally requires further processing, such as integration, to transform it into an integral film product.

As used herein the specification and the claims, the term "multilayered shaped film product" and variants thereof relate to thin products with two or more distinct layers (not mixed or homogeneous. Products with layers containing different characteristics such as: adhesion, flavor, color, texture, etc. Layers may be continuous, intermittent, or adjacent.

As used herein the specification and the claims, the term "tessellated" and variants thereof relate to a planar surface having a pattern of flat shapes having no overlaps or gaps. Thus, there is no "ladder waste between the shapes.

Figure 1:
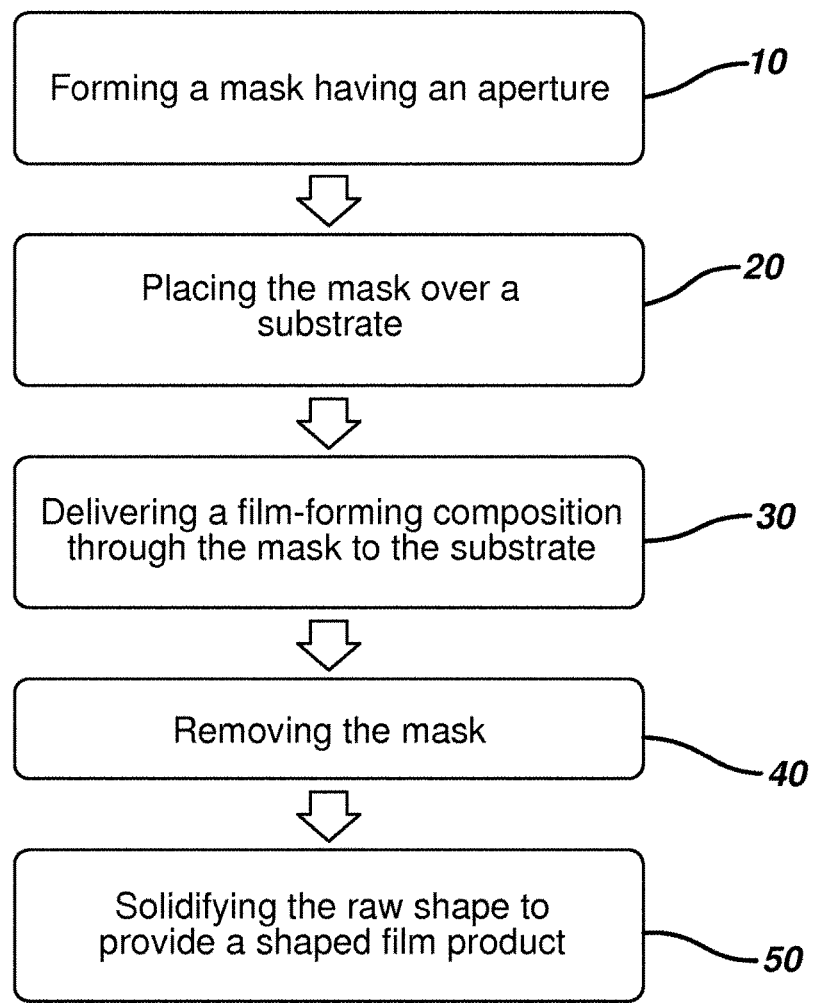
FIG. 1 is a block diagram of a process according to one embodiment of the present invention.

Referring to the drawing, FIG. 1 is a high level flow chart of a process for forming multilayered shaped film products. A first Step 10 includes forming a mask having an aperture. A second Step 20 includes placing the mask over a substrate. A third Step 30 includes delivering a liquid, film-forming composition through the mask to the substrate to form a raw shape. A fourth Step 40 includes removing the mask. A fifth Step 50 includes solidifying the raw shape to form the shaped film product.

Figure 2:
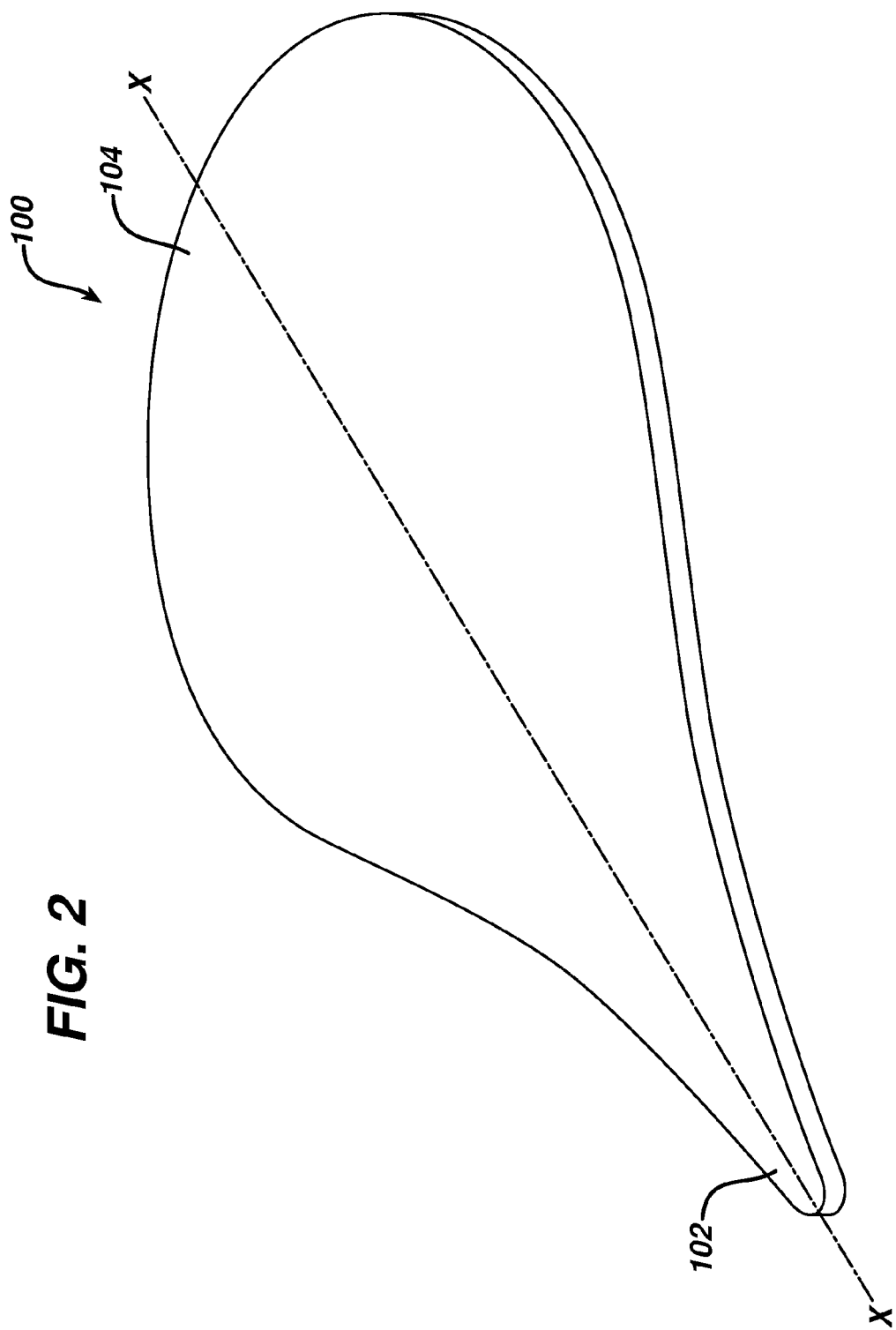
FIG. 2 is a perspective view of a shaped film product according to an embodiment of the present invention.

A shaped film product 100 according to one embodiment of the invention is shown in FIG. 2. In this embodiment, the shaped film product 100 has a variable width measured perpendicular to a longitudinal axis x-x, and the product is narrow at a first end 102, increases to a maximum width, and terminates with a rounded second end 104, opposite the first end 102.

As shown in FIG. 2, the innovations of the present invention allow the shape to be as simple or complex as desired. In one advantage of the present invention, the shape can be relatively complex—the kind of shape that would produce excessive ladder waste in a die-cutting operation. For example, the minimum ladder waste produced during the printing of a pattern of nested circles is about 20% (based on circles arranged in straight columns and rows touching at the quadrants).

In reference to the embodiment of FIG. 2, Step 10 involves forming a mask having at least one aperture corresponding to a raw shape.

Print masks are known in the art. They can include without limitation stencils, tapes, and the like. While the exact fabrication of the print masks is not critical to the present invention, our invention makes is possible to form relatively thick integral film products and therefore, use relatively thick masks. Preferably, the mask has a thickness of at least about 0.05 millimeters ("mm"). In one embodiment for use on the skin for flexible, relatively unnoticeable products, the mask has a thickness of between about 0.05 mm and about 0.3 mm, more preferably, between about 0.1 and about 0.2 mm. In another embodiment, thick integral film products can be made using a mask having a thickness of greater than about 0.2 mm, preferably between about 0.2 and about 2 mm, preferably between about 0.4 and about 1 mm, and most preferably between about 0.5 mm and about 1 mm. In many embodiments, the thickness of the mask is not critical, while in other embodiments, the present invention makes possible the formation of integral film products with previously unknown thicknesses.

The thickness of the mask generally determines the maximum thickness of the integral film product. The relationship is determined by the nature of the film-forming composition and the mechanism by which the composition solidifies. For example, hot melt and hydrocolloid film-forming compositions generally produce a product thickness that is essentially equivalent to the mask thickness. Foaming film-forming compositions can also be used and may provide solidified films having a thickness substantially equivalent to the thickness of the mask, or possibly even thicker. Solvent or other carrier-based compositions will lose thickness as the product solidifies. The reduction in thickness is generally related to the solids content of the composition. We have found that a solids content of 30-40% delivers an integral film product having a thickness of about 50% of the mask thickness. Formulations with lower solids content would likely deliver final products having a thickness of even less than 50% of the mask thickness.

For example, a stencil mask thickness of 0.5 mm would be capable of depositing a raw shape of film-forming composition of about 0.5 mm. Upon transformation into the integral film product, the thickness would diminish, based upon the solids content of the film-forming composition.

The choice of materials is not critical in the production of the print masks of the present invention. Those of ordinary skill in the art will recognize that masks can be made of structural materials, including without limitation: metals, such as aluminum alloy, stainless steel, Ni alloy, Cr alloy or the like; resins, such mask as polyimide, polyester, epoxy, polycarbonate, polyethylene, polyethylene terephthalate (PET), polypropylene or the like; glass; paper; wood; or cardboard, as well as combination thereof. As another example, the mask body may be made of a composite material, such as glass fiber filled polyimides, polyesters, or epoxies. The mask body is formed in a sheet from these materials. The thickness of the sheet may be from 20 to 2000 microns (µm), although for ease in handling and other considerations, the thickness is preferably from 20 to 80 µm.

In a preferred embodiment, the mask has a uniform thickness. However, it is possible to employ a mask having a thickness that changes along the machine direction. For example, the mask may have a thickened central portion along the machine direction and tapered ends.

Figure 3:
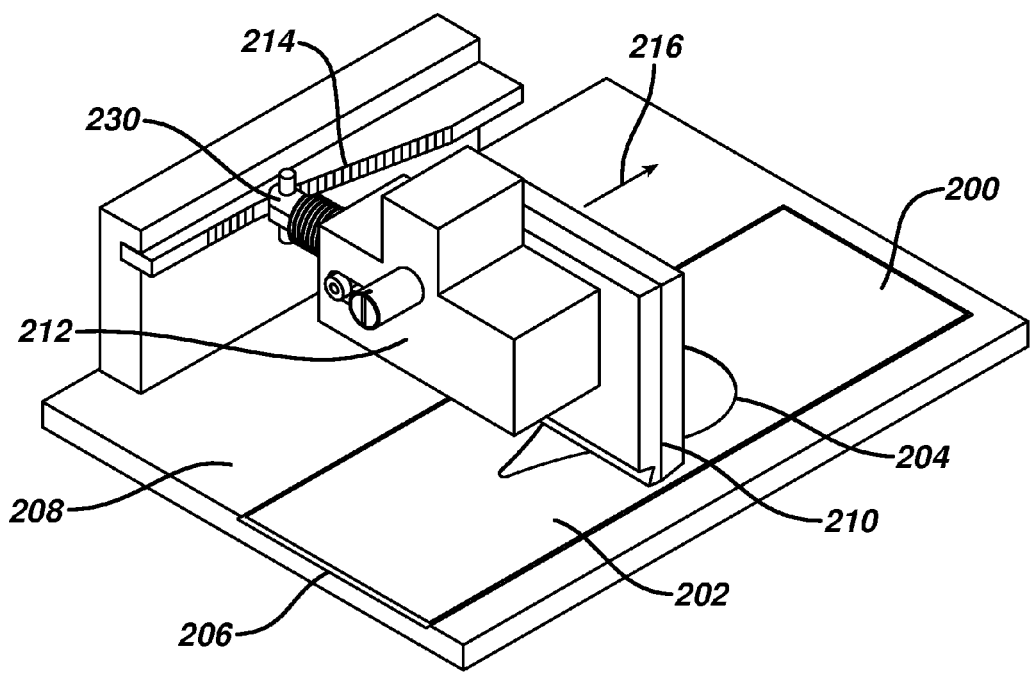
FIG. 3 is perspective view of a flatbed printing apparatus useful in one embodiment of the present invention.

An example of a mask according to one embodiment of the present invention, useful in the formation of the shaped film product 100 of FIG. 2 is a mask 200 that may be used in the flatbed printing apparatus shown in FIG. 3. The mask 200 includes an impermeable mask portion 202 which defines at least one aperture 204. The mask 200 is placed over a substrate 206 in Step 20. This substrate 206 may be an endless belt (a continuous flexible web, linked platens, and the like), or it may be a web that carries the resulting shaped product. The shaped product may be permanently attached to the web, or it may be releasably attached to a web, such as a release liner. Surfaces may be modified through the use of dry film lubricants such as molybdenum disulfide, graphite, tungsten disulfide or oils that are generally known to those of ordinary skill in the art. Typical release surfaces may include silicone, polytetrafluoroethylene (PTFE), waxes, polymers, polished metals, or combinations thereof. The process may employ flatbed apparatus or rotary apparatus. The printing apparatus will have a support 208 for the substrate 206 and system for delivering a film-forming composition through the mask aperture 204 (Step 30). The system includes a film-forming composition reservoir (not shown), a nozzle 210, a pump 212, and a pump controller (such as a cam 214).

The system for delivering the film-forming composition interacts with the mask 200 to provide appropriate volume of film-forming composition to the mask to accurately fill the void volume in the mask aperture 204 below the nozzle 210 during relative motion between the mask and nozzle. This relative motion (shown in FIGS. 3 and 4 as arrow 216) defines a machine direction.

Figure 4:
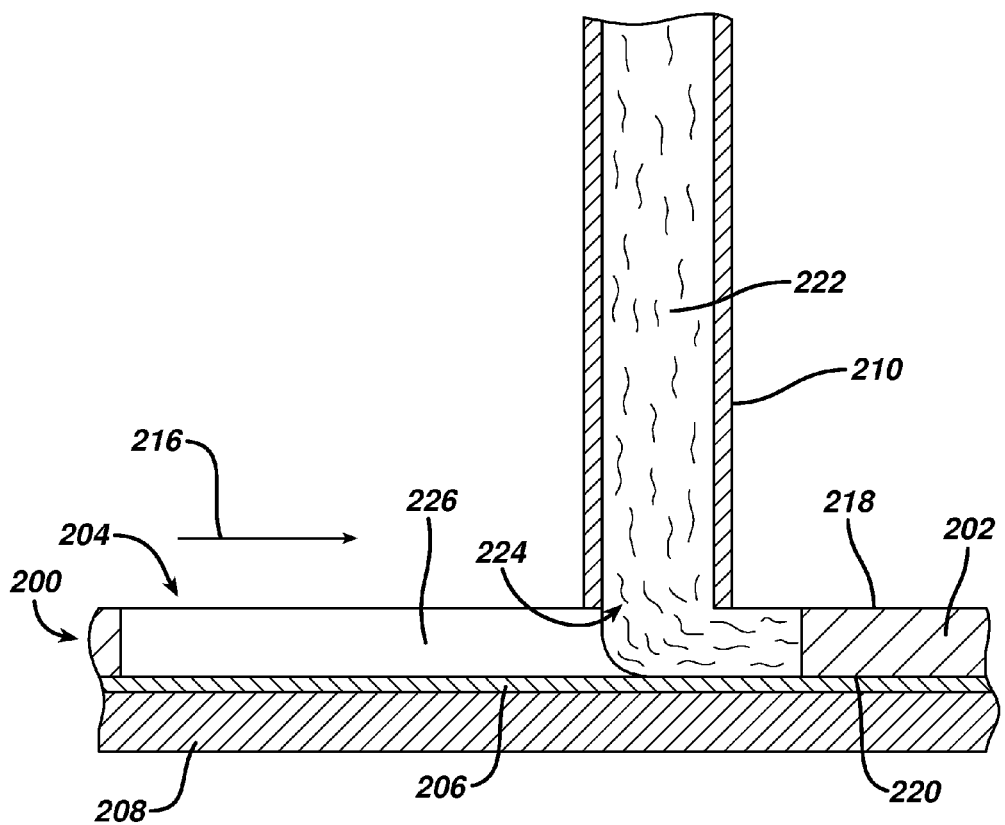
FIG. 4 is cross section of the apparatus of FIG. 3.

Referring to FIG. 4, the system includes a nozzle 210 arranged and configured bear against an upper surface 218 of the mask 200. The lower surface 220 of the mask 200 is in contact with the substrate 206. If the nozzle applies sufficient force against the substrate and mask, it will form a seal with the upper surface of the mask and between the lower surface and the substrate effective to minimize leakage of film-forming composition 222. The nozzle 210 has a delivery opening 224 defining a machine direction dimension and a cross-direction dimension. Preferably, the cross-direction dimension is greater than the maximum cross-direction dimension of the at least one aperture 204 formed in the mask 200, however, in some embodiments of the invention, the cross-direction dimension of the nozzle is equal to or slightly less than the maximum cross-direction dimension of the at least one aperture. Thus, the substrate 206, mask sidewalls 226 and the projection of the delivery opening 224 of the nozzle 210 define a void volume 228 when the nozzle is disposed over at least a portion of the mask aperture 204, and the pump is controlled to output a volume of the film-forming composition 222 to the delivery opening 224 corresponding to that void volume over which the delivery opening 224 is located. This void volume can change during the relative motion between the nozzle 210 and mask 200, so the volume of the film-forming composition output to the delivery opening 224 will change with the changing void volume. The output of the pump 212 can be controlled through control means known to those of ordinary skill in the art. In an example shown in FIG. 3, the mask 200 can be placed in proximity to a cam 214 that is coupled to a piston pump form of a positive displacement pump 212. In this arrangement, the nozzle 210 is movable across the upper surface 218 of the mask 200 defining the mask aperture 204. The nozzle 210 is connected to a positive displacement pump 212 having a cavity or bore containing the film-forming composition 222. As the nozzle 210 reaches the mask aperture 204 a cam follower 230 engages the cam 214. The cam profile correlates to the void volume defined by the substrate 206, mask sidewalls 226 and delivery opening 224 of the nozzle 210, as described above. As the nozzle 210 moves along the mask 200, the cam 214 determines the motion of the cam follower 230 to move a piston in the bore of the pump to output a volume of film-forming material 222 corresponding to the void volume adjacent the delivery opening 224 of the nozzle 210. Because the output volumetric flow of the positive displacement pump 212 corresponds to the changing void volume as the nozzle 210 moves along the mask 200, there is minimal disturbance to fluid flow. Preferably, the flow is substantially laminar from the delivery opening to the substrate. When the delivery opening 224 of the nozzle 210 reaches the end of the mask aperture 204, the pump output terminates, and the film-forming composition delivery system may then be removed from the mask. The delivery opening 224 may have any shape appropriate for delivering the film-forming composition. A particularly preferred delivery opening is a rectangular slot having a cross-direction dimension that is substantially greater than the machine direction dimension.

Figure 5A:
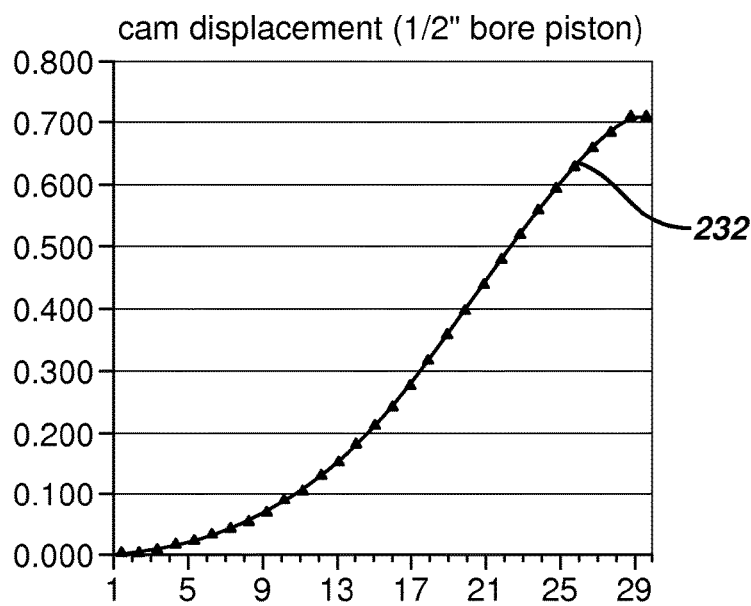
FIG. 5A is a graph of the displacement of a piston in the bore of the positive displacement pump of FIG. 3.
Figure 5B:
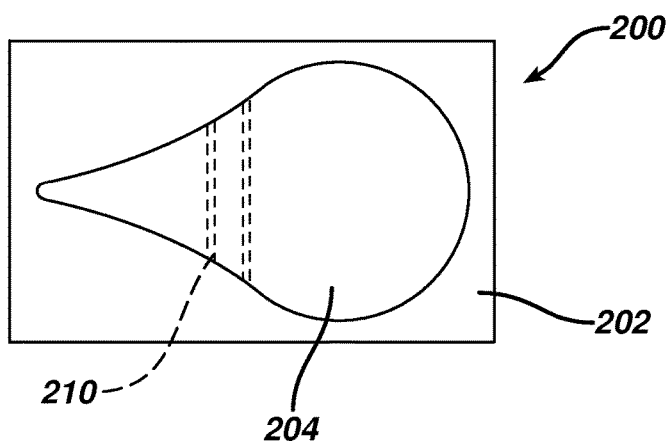
FIG. 5B is a plan view of a mask correlated to the displacement of the piston in the bore of the positive displacement pump of FIG. 3.

Using a rectangular slot nozzle, the cam displacement for a teardrop-shaped film product having a raw shape thickness of about 0.75 mm is shown in FIGS. 5A and 5B. FIG. 5A shows a graph of the displacement of the cam follower 230 that is coupled to a piston having a ½ inch diameter in the bore of the positive displacement pump 212 of FIG. 3. FIG. 5B is a plan view of a mask 200 correlated to the displacement of the cam follower 230 caused by movement along the cam 214 in the direction shown in FIG. 4. A comparison of FIGS. 5A and 5B shows that no film-forming composition is provided to the mask aperture until the nozzle reaches the left edge of the mask aperture. Thus, the slope of the displacement line 232 is zero at the right edge of the graph of FIG. 5A. The volumetric flow rate increases as the aperture width increases (shown by the greater slope of displacement line 232 of FIG. 5A). Once the maximum width of the mask aperture is reached near a value of about 20 on the x-axis of FIG. 5A, the volumetric flow rate decreases to zero at the right edge of the mask aperture.

While the above process is described with respect to a cam system controlling a positive displacement pump, it is evident that alternative volumetric pumps and volumetric flow controllers may be used and correlated to the relative motion of the nozzle and mask aperture. For example, computer controlled volumetric pumps can vary the fluid dispense rate to portions of the mask aperture to provide the volume of film-forming composition corresponding to the void volume. Additional, non-limiting representative examples of such pumps and controls include rotary pumps (such as gear, screw, peristaltic, and flexible impeller) and reciprocating pumps (such as piston and diaphragm), and the like.

In step 40, the first mask 200 is removed leaving a first raw shape deposited on the substrate 206. The faster the mask is removed, the better the definition and edge quality of the raw shape and resulting film product. Thus, a rotary stencil generally delivers a superior quality shaped film product.

In step 50, the raw shape 234 is solidified into the shaped film product 100. Again, the shaped film product 100 may be permanently attached to the substrate 206, or the substrate 206 may be a release liner to permit the product to be removed therefrom for use independent of the substrate. The exact nature of the solidifying station is not critical to the present invention. For example, the raw shape may be heated to drive off volatile carriers, such as such as water and organic solvents. Alternately, the solidifying can be through providing energy, such as UV light to cross-link or otherwise "cure" one or more polymeric film-forming components. If one or more film-forming components is a hotmelt composition, the solidifying can be as simple as allowing the raw shape to cool below a melt or glass transition temperature.

One of ordinary skill in the art will recognize that additional layers may be added by repeating steps 20 through 40 with additional film-forming compositions to provide multilayered film products (without solidification between film layer formation) having at least two layers. The present invention is particularly suited to apply raw shapes in layers as there is minimal disturbance to fluid flow with the correlated volumetric output of the pump, as described above. Again, multiple layers formed on raw, unsolidified layers are possible, because the delivery of subsequent layers occurs with substantially laminar flow. This minimizes mixing of adjacent film-forming compositions. Accurate control of the nozzle output avoids layer mixing at the point of application.

Again, the shaped film product may be permanently attached to the web, or it may be releasably attached to a web, such as a release liner. If the process according to the present invention employs a release lined web as the substrate, the release lined web may be used as a carrier and packaged with the shaped film product in appropriate sized primary packaging until delivered to a consumer. The consumer may then remove the shaped film product from the substrate and use it as desired. Alternately, if the process according to the present invention employs an endless belt having a releasable surface or other substrate integrated into the manufacturing equipment, the shaped film product is removed from the releasable surface of the substrate and packaged for delivery to a consumer. The shaped film product may have an adhesive surface, such as in a medicated plaster, or it may have non-tacky surfaces, such as in an oral strip.

Figure 6:
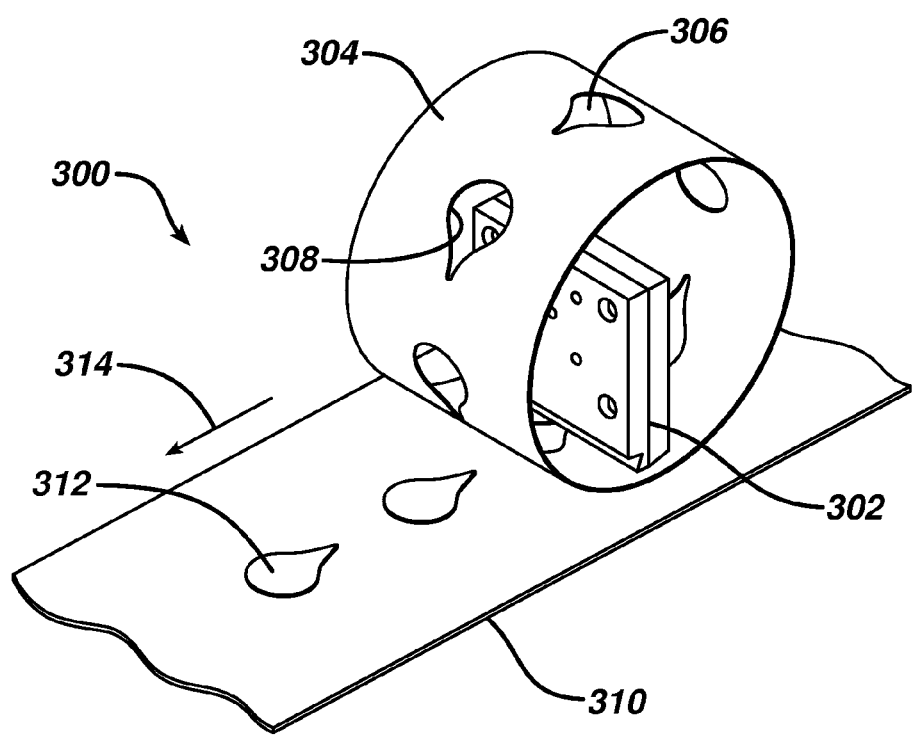
FIG. 6 is perspective view of a rotary printing system useful in an alternate embodiment of the present invention.

The above processes are described with reference to flatbed stencil printing systems. However, one of ordinary skill in the art will recognize that variations may be made to the process. For example, a rotary printing system 300 shown in FIG. 6 may be used. In this system, the film-forming composition is applied with a nozzle 302. A printing drum 304 includes a plurality of mask apertures 306. The rotation of the drum 304 indexes a mask aperture 306 to the nozzle 302. A controller, such one or more elements to identify and read mask aperture position, correlates the controlled volumetric delivery of film-forming composition to the delivery opening of the nozzle (as described above). The film-forming composition is delivered to the interior of the drum 304 via a conduit from a reservoir (not shown) void volume defined by the nozzle 302, mask sidewalls 308 and substrate 310, again, as described above. The raw shape 312 then moves in the direction of arrow 314 for further processing.

The following technical considerations are believed to be relevant to stencil printing via a film-forming composition delivery nozzle. Accurate dispensing of the film-forming composition leads to successful accurate shape formation. This is achieved when the instantaneous volume of the film-forming composition dispensed equals the immediately adjacent and corresponding stencil volume. In the undesirable event of dispensing excess film-forming composition, the excess collects on the leading edge of the slot nozzle. This accumulation can spill uncontrollably through the next stencil opening and contaminate the exterior surface of the stencil. This creates defects such as poor edge definition and smears between patterns. Under filling of the mask aperture leads to product defects such as skips and voids. The slot nozzle opening (width) generally equals the maximum pattern width. Pressing the nozzle against the stencil surface creates a dynamic seal. Hence, the effective nozzle width naturally changes as the stencil opening passes across the nozzle.

Capillary action can draw the liquid film-forming composition into narrow gaps. Stenciling in a flat plane works best with the quick removal of the stencil from the substrate to avoid liquid wicking between. Capillary action can create defects such as feathered and rough edges. Rotary stenciling (stencil in a cylinder form) minimizes the effects of capillary action, because stencil contact with the substrate is along a line tangent to the cylindrical. Increasing web (substrate) speed can improve this further.

Print thickness is controlled by mask thickness (and the corresponding liquid flow). The minimum mask thickness is a material strength issue. Stainless steel 0.006 inch thick may be a practical lower limit with current technology. 0.006 thick mask yields dry film thicknesses in the range of 0.002-0.003 inch depending upon liquid solids content.

Figure 7A:
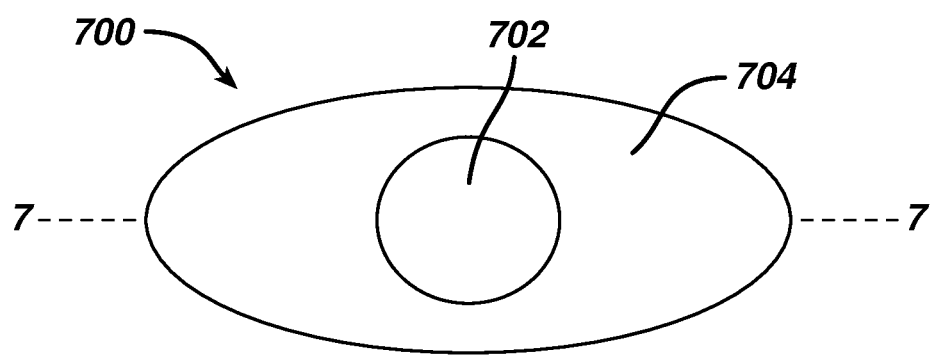
FIG. 7A is a bottom plan view of a multicomponent shaped film product according to an alternate embodiment of the invention.
Figure 7B:
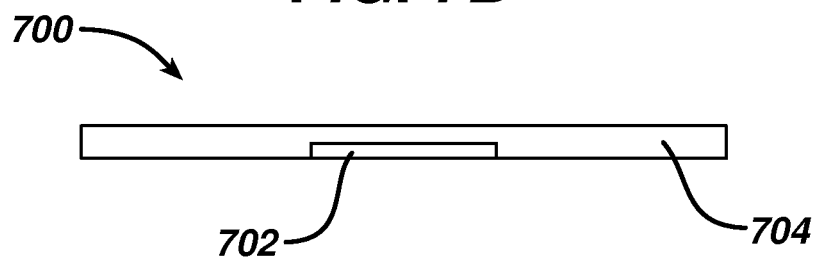
FIG. 7B is a cross-section of the multilayer film product of FIG. 7A along line 7-7.
Figure 8:
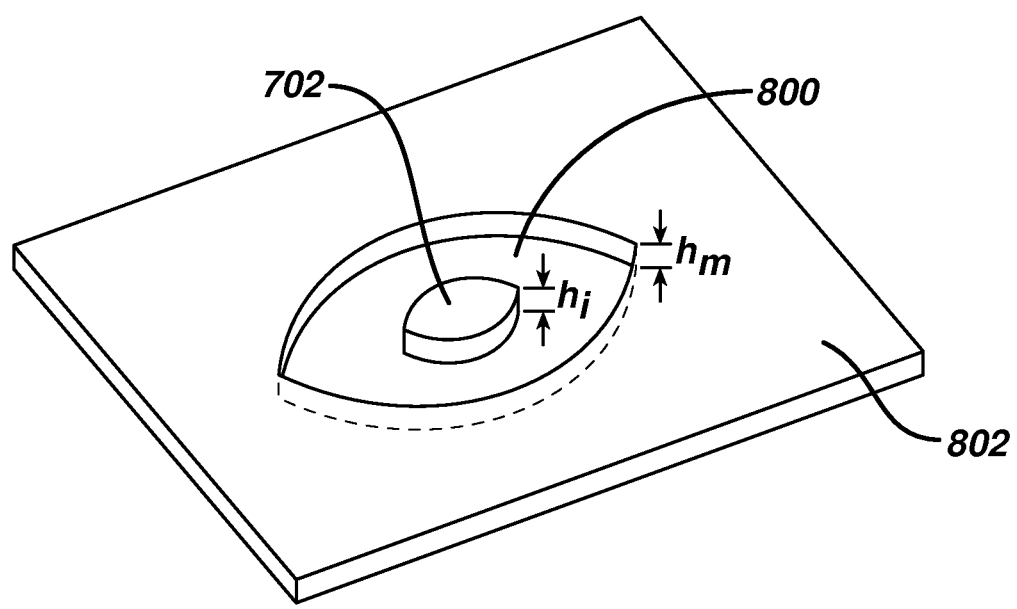
FIG. 8 is a perspective view of a step in the formation of the multicomponent shaped film product of FIG. 7A.

Island stencil printing offers special challenges due to the above considerations. Stencil printing of a multicomponent shaped film product 700 having an island 702 surrounded by another film material 704 (such as shown in FIGS. 7A and B) according to the present invention takes advantage of the laminar flow of the film-forming composition during printing. The "film material(s)" are the result of the transformation of the film-forming composition(s) into a film structure. This also avoids mixing between layers. In order to form a stencil-printed "island" product 700, the island portion 702 of the product can be formed on the substrate 800 as an initial step (as shown in FIG. 8). This initial step can be performed via stencil printing as described above, or it can be formed otherwise, such as via screen printing, and other processes know to those of ordinary skill in the art. Next, a mask 802 is placed about the "island", and the aperture of the mask is filled with a film-forming composition as described above (see FIGS. 3 and 4), however, the dispensing flow rate must account for the island volume. When calculating the instantaneous dispense rate the island volume would be subtracted from the total volume. It is also important that the shape of the island corresponds to or fits within the mask aperture and has a height $h_i$ that is less than the thickness of the mask $h_m$. Again, accurate flow rate of the film-forming composition is important to avoid smearing and or mixing of the island layer by the subsequently added top layer.

We have also found that it is preferred to have an island film-forming composition viscosity higher than the second film-forming composition viscosity. The higher viscosity will better resist sheer forces and discourage mixing.

The film-forming compositions employed in the present invention may be in the form of a hotmelt composition, a solid material that can be melted to form a flowable liquid and deposited to form a raw shape which can then cool to form the integral film product. Alternatively, the film-forming composition may include at least a film forming component and a carrier. Additional components may include, without limitation, emulsifiers, surfactants, plasticizers, active ingredients, fragrances, coloring agents, flavorings, and other components known to those of ordinary skill in the art. The carrier is preferably a liquid and may be a solvent or diluent. Preferred carriers include water and alcohols.

The water soluble polymers of the present invention possess film forming properties useful producing the films of the present invention. Many water soluble polymers may be used in the films of the present invention. A representative, non-limiting list includes pullulan, cellulose ethers (such as hydroxypropylmethyl cellulose, hydroxyethyl cellulose, hydroxypropyl cellulose), polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymers, carboxyvinyl polymers, amylose, starches (such as high amylose starch and hydroxypropylated high amylose starch), dextrin, pectin, chitin, chitosan, levan, elsinan, collagen, gelatin, zein, gluten, soy protein isolate, whey protein isolate, casein and/or mixtures thereof.

In one preferred embodiment, the carrier is water. In alternate embodiments, organic solvents which have been conventionally used can be employed as the solvent. A representative, non-limiting list of useful solvents includes monovalent alcohols such as methanol, ethanol, propanol, butanol, 3-methoxy-3-methyl-1-butanol, and 3-methoxy-1-butanol; alkylcarboxylic acid esters such as methyl-3- methoxypropionate, and ethyl-3-ethoxypropionate; polyhydric alcohols such as ethylene glycol, diethylene glycol, and propylene glycol; polyhydric alcohol derivatives such as ethylene glycol monomethyl ether, ethylene glycol monoethyl ether, ethylene glycol monopropyl ether, ethylene glycol monobutyl ether, propylene glycol monomethyl ether, propylene glycol monoethyl ether, propylene glycol monopropyl ether, propylene glycol monobutyl ether, ethylene glycol monomethyl ether acetate, ethylene glycol monoethyl ether acetate, and propylene glycol monomethyl ether acetate; fatty acids such as acetic acid, and propionic acid; ketone such as acetone, methyl ethyl ketone, and 2-heptanone. These organic solvents may be used alone, or in combination.

The film product may also contain at least one surfactant, including anionic, amphoteric, non-ionic, and cationic surfactants or mixtures thereof.

A representative, non-limiting list of anionic surfactants includes, alone or mixed, salts (for example salts of alkali metals, such as of sodium, ammonium salts, salts of amines, salts of amino-alcohols or magnesium salts) of the following compounds: alkyl sulphates, alkylether sulphates, alkylamidoether-sulphates, alkylarylpolyether-sulphates, monoglyceride sulphates, alkyl sulphonates, alkyl phosphates, alkylamide sulphonates, alkaryl sulphonates, alpha-olefin sulphonates, paraffin sulphonates; alkyl sulphosuccinates, alkylether sulphosuccinates, alkylamide-sulphosuccinates, alkyl sulphosuccinamates, alkyl sulphoacetates, alkylether phosphates, acyl sarcosinates, acyl isethionates and N-acyl taurates, the alkyl or acyl radical of all these various compounds for example having from 8 to 24 carbon atoms, and an aryl radical such as a phenyl or benzyl group.

According to at least one embodiment, the salts include those of fatty acids, such as the salts of oleic, ricinoleic, palmitic, stearic acids, acids of copra oil or of hydrogenated copra oil, acyl lactylates whose acyl radical has 8 to 20 carbon atoms, alkyl D-galactoside uronic acids and their salts as well as the polyoxyalkylenated alkyl(C6-C24)ether carboxylic acids, the polyoxyalkylenated alkyl(C6-C24)aryl ether carboxylic acids, the polyoxyalkylenated alkyl(C6-C24)amido-ether carboxylic acids and their salts, for example those having from 2 to 50 ethylene oxide groups, and mixtures thereof.

A representative, non-limiting list of amphoteric surfactants includes, alone or mixed, the derivatives of secondary or tertiary aliphatic amines wherein the aliphatic radical is a linear and branched chain with 8 to 22 carbon atoms and comprises at least one hydrosolubilizing anionic group (for example carboxylate, sulphonate, sulphate, phosphate or phosphonate); the alkyl (C8-C20) betaines, the sulphobetaines, the alkyl (C8-C20) amidoalkyl (C1-C6) betaines such as cocoamidopropyl betaine or the alkyl (C8-C20) amidoalkyl (C1-C6) sulphobetaines.

A representative, non-limiting list of non-ionic surfactants includes, alone or mixed, alcohols, alpha-diols, alkyl phenols or polyethoxylated, polypropoxylated or polyglycerolated fatty acids, having an aliphatic chain with for example 8 to 18 carbon atoms, where the number of ethylene oxide or propylene oxide groups can optionally be in the range from 2 to 50 and the number of glycerol groups can optionally be in the range from 2 to 30.

Any plasticizer known in the pharmaceutical art is suitable for use in the film product. These include, but are not limited to, polyethylene glycol; glycerin; sorbitol; triethyl citrate; tribuyl citrate; dibutyl sebecate; vegetable oils such as castor oil; surfactants such as polysorbates, sodium lauryl sulfates, and dioctyl-sodium sulfosuccinates; propylene glycol; mono acetate of glycerol; diacetate of glycerol; triacetate of glycerol; natural gums and mixtures thereof.

The film product of the present invention may also contain at least one colorant, such as a pigment or dyestuff. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the cosmetic compositions of the invention will depend on the color, intensity and use of the cosmetic composition and, as a result, will be determined by those skilled in the art of cosmetic formulation.

Any thickener known in the art may optionally be added to the film. Suitable thickeners include, but are not limited to, cyclodextrin, crystallizable carbohydrates, and the like, and derivatives and combinations thereof. Suitable crystallizable carbohydrates include the monosaccharides and the oligosaccharides. Of the monosaccharides, the aldohexoses e.g., the D and L isomers of allose, altrose, glucose, mannose, gulose, idose, galactose, talose, and the ketohexoses e.g., the D and L isomers of fructose and sorbose along with their hydrogenated analogs: e.g., glucitol (sorbitol), and mannitol are preferred. Of the oligosaccharides, the 1,2-disaccharides sucrose and trehalose, the 1,4-disaccharides maltose, lactose, and cellobiose, and the 1,6-disaccharides gentiobiose and melibiose, as well as the trisaccharide raffinose are preferred along with the isomerized form of sucrose known as isomaltulose and its hydrogenated analog isomalt. Other hydrogenated forms of reducing disaccharides (such as maltose and lactose), for example, maltitol and lactitol are also preferred. Additionally, the hydrogenated forms of the aldopentoses: e.g., D and L ribose, arabinose, xylose, and lyxose and the hydrogenated forms of the aldotetroses: e.g., D and L erythrose and threose are suitable and are exemplified by xylitol and erythritol, respectively.

Preservatives known in the art may optionally be added to the film. Suitable Preservatives include, but are not limited to Benzalkonium Chloride, Benzyl Alcohol, 2-Bromo-2-Nitropropane, Butylparaben, Chlorhexidine Digluconate, Chlorphenism, Dehydroacetic Acid, Citric Acid, Diazolidinyl Urea, DMDM Hydantoin, Ethylparaben, Formaldahyde, Imidazolidinyl Urea, Isobutylparaben, Methylisothiazolinone, Methylparaben, Phenoxyethanol, Polyaminopropyl biguanide, Potassium Sorbate, Propylparaben, Quaternium-15, Salicylic Acid, Sodium benzoate, Sodium Dehydroacetate, Sodium Metabisulfite, Sodium Salicylate, Sodium Sulfite, Sorbic Acid, Stearalkonium Chloride, Triclosan, and Zinc Pyrithione.

In some embodiments, "microbeads" or other particulate materials may be incorporated and used as "scrubbing particles" or "exfoliates" in film products used in personal care products such as facial scrubs and body washes. The microbeads are small particles, generally having a particle size of less than about 1,000 µm, often less than about 750 µm. Often, topical compositions and/or skin cleansing compositions incorporate microbeads or particulates having a size of less than about 300 µm, and preferably, less than about 100 µm. Particulates, such as pumice can range from 35-1400 µm; topical compositions generally employ pumice having a particle size of about 100 µm. The microbeads can be a generally homogeneous material and can comprise pumice, polyethylene, glass, aluminum oxide, titanium dioxide, celluloses, such as Hydroxypropyl Methylcellulose (HPMC), or Vitamin E. Alternatively, the microbeads can be in the form of microencapsulated particles in which desirable material is encapsulated in a covering material to delay the release of the material to the environment. The microencapsulated particle may include adhesives and/or one or more benefit agents described in more detail below.

In a preferred embodiment, the film-forming composition, for example as shown in FIGS. 2 and 3, includes a benefit agent. The resulting shaped film product 100 has a first surface 106 formed on a releasable surface of the substrate, and a second surface 108 opposite thereof. The first surface 106 is arranged and configured to deliver the benefit agent therethrough. For example, the first surface 106 may be protected by a release liner on a flexible substrate during manufacture and storage prior to use by a consumer. On the other hand, the second surface 108 is exposed to ambient conditions during the finishing of the raw shape. Thus, the first surface 106 may be tacky after removal from the substrate, and it may adhere to the skin of a consumer. The second surface 108 may "dry out" during transformation to the shaped film product 100. Thus, the tacky first surface 106 can be ideal for delivery of a benefit agent to the skin of the consumer.

As used herein the specification and the claims, the term "benefit agent" and variants thereof relates to an element, an ion, a compound (e.g., a synthetic compound or a compound isolated from a natural source) or other chemical moiety in solid (e.g. particulate), liquid, or gaseous state and compound that has a cosmetic or therapeutic effect on the skin.

The compositions of the present invention may further include one or more benefit agents or pharmaceutically-acceptable salts and/or esters thereof, the benefit agents generally capable of interacting with the skin to provide a benefit thereto. As used herein, the term "benefit agent" includes any active ingredient that is to be delivered into and/or onto the skin at a desired location, such as a cosmetic or pharmaceutical.

The benefit agents useful herein may be categorized by their therapeutic benefit or their postulated mode of action. However, it is to be understood that the benefit agents useful herein may, in some circumstances, provide more than one therapeutic benefit or operate via greater than one mode of action. Therefore, the particular classifications provided herein are made for the sake of convenience and are not intended to limit the benefit agents to the particular application(s) listed.

Examples of suitable benefit agents include those that provide benefits to the skin, such as, but not limited to, depigmentation agents; reflectants; film forming polymers; amino acids and their derivatives; antimicrobial agents; allergy inhibitors; anti-acne agents; anti-aging agents; anti-wrinkling agents, antiseptics; analgesics; shine-control agents; antipruritics; local anesthetics; anti-hair loss agents; hair growth promoting agents; hair growth inhibitor agents, antihistamines; anti-infectives; anti-inflammatory agents; anticholinergics; vasoconstrictors; vasodilators; wound healing promoters; peptides, polypeptides and proteins; deodorants and antiperspirants; medicament agents; skin firming agents, vitamins; skin lightening agents; skin darkening agents; antifungals; depilating agents; counterirritants; hemorrhoidals; insecticides; enzymes for exfoliation or other functional benefits; enzyme inhibitors; poison ivy products; poison oak products; burn products; anti-diaper rash agents; prickly heat agents; vitamins; herbal extracts; vitamin A and its derivatives; flavenoids; sensates; antioxidants; hair lighteners; sunscreens; anti-edema agents, neo-collagen enhancers, film-forming polymers, chelating agents; anti-dandruff/sebhorreic dermatitis/psoriasis agents; keratolytics; and mixtures thereof.

In addition the benefit agent may also provide passive benefits to the skin. As such, the benefit agent may be formulated into a composition that include such ingredients as humectants or emollients, softeners or conditioners of the skin, make-up preparations, and mixtures thereof.

Examples of suitable anti-edema agents nonexclusively include bisabolol natural, synthetic bisabolol, corticosteroids, beta-glucans, and mixtures thereof.

Examples of suitable vasoconstrictors nonexclusively include horse chestnut extract, prickly ash, peroxides, tetrahydrozaline, and mixtures thereof.

Examples of suitable anti-inflammatory agents nonexclusively include benoxaprofen, centella asiatica, bisabolol, feverfew (whole), feverfew (parthenolide free), green tea extract, green tea concentrate, hydrogen peroxide, salicylates, oat oil, chamomile, and mixtures thereof.

Examples of neo-collagen enhancers nonexclusively include vitamin A and its derivatives (e.g. beta-carotene and retinoids such as retinoic acid, retinal, retinyl esters such as and retinyl palmitate, retinyl acetate and retinyl propionate); vitamin C and its derivatives such as ascorbic acid, ascorbyl phosphates, ascorbyl palmitate and ascorbyl glucoside; copper peptides; simple sugars such as lactose, mellibiose and fructose; and mixtures thereof.

Examples of enzymes include papain, bromelain, pepsin, and trypsin.

Examples of suitable skin firming agent nonexclusively include alkanolamines such as dimethylaminoethanol ("DMAE").

Examples of suitable antipruritics and skin protectants nonexclusively include oatmeal, beta-glucan, feverfew, soy products (by "soy product," it is meant a substance derived from soybeans, as described in United States Patent Application 2002-0160062), bicarbonate of soda, colloidal oatmeal, *Anagallis Arvensis, Oenothera Biennis, Verbena Officinalis*, and the like. As used herein, colloidal oatmeal means the powder resulting from the grinding and further processing of whole oat grain meeting United States Standards for Number 1 or Number 2 oats. The colloidal oatmeal has a particle size distribution as follows: not more than 3 percent of the total particles exceed 150 micrometers in size and not more than 20 percent of the total particles exceed 75 micrometers in size. Examples of suitable colloidal oatmeals include, but are not limited to, "Tech-O" available from the Beacon Corporation (Kenilworth, N.J.) and colloidal oatmeals available from Quaker (Chicago, Ill.).

Examples of suitable reflectants nonexclusively include mica, alumina, calcium silicate, glycol dioleate, glycol distearate, silica, sodium magnesium fluorosilicate, and mixtures thereof.

Examples of skin darkening agents nonexclusively include dihydroxy acetone, erythulose, melanin, and mixtures thereof.

Suitable film forming polymers include those that, upon drying, produce a substantially continuous coating or film on the skin or nails. Nonexclusive examples of suitable film forming polymers include acrylamidopropyl trimonium chloride/acrylamide copolymer; corn starch/acrylamide/sodium acrylate copolymer; polyquaternium-10; polyquaternium-47; polyvinylmethylether/maleic anhydride copolymer; styrene/acrylates copolymers; and mixtures thereof.

Commercially available humectants which are capable of providing moisturization and conditioning properties nonexclusively include: (i) water soluble liquid polyols selected from the group comprising glycerine, propylene glycol, hexylene glycol, butylene glycol, pentylene glycol, dipropylene glycol, and mixtures thereof; (ii) polyalkylene glycol of the formula HO—(R"O)b-H wherein R" is an alkylene group having from about 2 to about 4 carbon atoms and b is an integer of from about 1 to about 10, such as PEG 4; (iii) polyethylene glycol ether of methyl glucose of formula CH3-C6H10O5-(OCH2CH2)c-OH wherein c is an integer from about 5 to about 25; (iv) urea; (v) fructose; (vi) glucose; (vii) honey; (viii) lactic acid; (ix) maltose; (x) sodium glucuronate; and (xi) mixtures thereof, with glycerine being an exemplary humectant.

Suitable amino acids and derivatives include amino acids derived from the hydrolysis of various proteins as well as the salts, esters, and acyl derivatives thereof. Examples of such amino acid agents nonexclusively include amphoteric amino acids such as alkylamido alkylamines, i.e. stearyl acetyl glutamate, caproyl silk amino acid, caproyl collagen amino acids; caproyl keratin amino acids; caproyl pea amino acids; cocodimonium hydroxypropyl silk amino acids; corn gluten amino acids; cysteine; glutamic acid; glycine; hair keratin amino acids; amino acids such as aspartic acid, threonine, serine, glutamic acid, proline, glycine, alanine, cystine, valine, methionine, isoleucine, leucine, tyrosine, phenylalanine, cysteic acid, lysine, histidine, arginine, cysteine, tryptophan, citrulline; lysine; silk amino acids, wheat amino acids; and mixtures thereof.

Suitable proteins include those polymers that have a long chain, i.e. at least about 10 carbon atoms, and a high molecular weight, i.e. at least about 1000, and are formed by self-condensation of amino acids. Nonexclusive examples of such proteins include collagen, deoxyribonuclease, iodized corn protein; milk protein; protease; serum protein; silk; sweet almond protein; wheat germ protein; wheat protein; alpha and beta helix of keratin proteins; hair proteins, such as intermediate filament proteins, high-sulfur proteins, ultra-high-sulfur proteins, intermediate filament-associated proteins, high-tyrosine proteins, high-glycine tyrosine proteins, tricohyalin, and mixtures thereof.

Examples of suitable vitamins nonexclusively include various forms of vitamin B complex, including thiamine, nicotinic acid, biotin, pantothenic acid, choline, riboflavin, vitamin B3, vitamin B6, vitamin B12, pyridoxine, inositol, carnitine; vitamins A,C,D,E,K and their derivatives such as vitamin A palmitate and pro-vitamins, e.g. (i.e., panthenol (pro vitamin B5) and panthenol triacetate) and mixtures thereof.

Examples of suitable antimicrobial agents nonexclusively include bacitracin, erythromycin, neomycin, tetracycline, chlortetracycline, benzethonium chloride, phenol, benzyl peroxide, metal salts or ions such as silver and its salts and mixtures thereof.

Examples of suitable skin emollients and skin moisturizers nonexclusively include mineral oil, lanolin, vegetable oils, isostearyl isostearate, glyceryl laurate, methyl gluceth-10, methyl gluceth-20 chitosan, and mixtures thereof.

An example of a suitable hair softener nonexclusively includes silicone compounds, such as those that are either non-volatile or volatile and those that are water soluble or water insoluble. Examples of suitable silicones include organo-substituted polysiloxanes, which are either linear or cyclic polymers of monomeric silicone/oxygen monomers and which nonexclusively include cetyl dimethicone; cetyl triethylammonium dimethicone copolyol phthalate; cyclomethicone; dimethicone copolyol; dimethicone copolyol lactate; hydrolyzed soy protein/dimethicone copolyol acetate; silicone quaternium 13; stearalkonium dimethicone copolyol phthalate; stearamidopropyl dimethicone; and mixtures thereof.

Examples of sunscreens, nonexclusively include benzophenones, bornelone, butyl paba, cinnamidopropyl trimethyl ammonium chloride, disodium distyrylbiphenyl disulfonate, PABA and its derivatives (such as octyl dimethyl PABA, butyl methoxydibenzoylmethane, isoamyl methoxycinnamate, methyl benzilidene camphor, octyl triazole, octyl methoxycinnamate, oxybenzone, octocrylene, octyl salicylate, homosalate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, Padimate O, red petrolatum, MEXORYL S and SX, TINOSORB M and S, and mixtures thereof.

Examples of skin lightening agents nonexclusively include hydroquinone, catechol and its derivatives, ascorbic acid and its derivatives, and mixtures thereof.

Examples of suitable insecticides (including insect repellents, anti-scabies and anti-lice treatments) nonexclusively include permethrin, pyrethrin, piperonyl butoxide, imidacloprid, N,N-diethyl toluamide, which refers to the material containing predominantly the meta isomer, i.e., N,N-diethyl-m-toluamide, which is also known as DEET, natural or synthetic pyrethroids, whereby the natural pyrethroids are contained in pyrethrum, the extract of the ground flowers of *Chrysanthemum cinerariaefolium* or *C. coccineum*; and mixtures thereof. Within the structure of Formula III, are ethyl 3-(N-butylacetamido)propionate, wherein R7 is a CH3 group, R5 is an n-butyl group, R6 is H, K is COOR8 and R8 is ethyl, which is available commercially from Merck KGaA of Darmstadt, Germany under the name, "Insect Repellent 3535."

Examples of an anti-fungal for foot preparations nonexclusively include tolnaftate and myconozole.

Examples of suitable depilating agents nonexclusively include calcium thioglycolate, magnesium thioglycolate, potassium thioglycolate, strontium thioglycolate, and mixtures thereof.

Examples of suitable analgesics such as external analgesics and local anesthetics nonexclusively include benzocaine, dibucaine, benzyl alcohol, camphor, capsaicin, *capsicum, capsicum* oleoresin, juniper tar, menthol, methyl nicotinate, methyl salicylate, phenol, resorcinol, turpentine oil, and mixtures thereof.

Examples of suitable antiperspirants and deodorants nonexclusively include aluminium chlorohydrates, aluminium zirconium chlorohydrates, and mixtures thereof.

Examples of suitable counterirritants nonexclusively include camphor, menthol, methyl salicylate, peppermint and clove oils, ichtammol, and mixtures thereof.

An example of a suitable inflammation inhibitor nonexclusively includes hydrocortisone, *Fragaria Vesca, Matricaria Chamomilla,* and *Salvia Officinalis.*

Examples of suitable anaesthetic ingredients nonexclusively include the benzocaine, pramoxine hydrochloride, lidocaine, betacaine and mixtures thereof; antiseptics such as benzethonium chloride; astringents such as zinc oxide, bismuth subgallate, balsam Peru, and mixtures thereof; skin protectants such as zinc oxide, silicone oils, petrolatum, cod liver oil, vegetable oil, and mixtures thereof.

Examples of such suitable benefits agents effective in the treatment of dandruff, seborrheic dermatitis, and psoriasis, as well as the symptoms associated therewith nonexclusively include zinc pyrithione, anthralin, shale oil and derivatives thereof such as sulfonated shale oil, selenium sulfide, sulfur; salicylic acid; coal tar; povidone-iodine, imidazoles such as ketoconazole, dichlorophenyl imidazolodioxalan ("elubiol"), clotrimazole, itraconazole, miconazole, climbazole, tioconazole, sulconazole, butoconazole, fluconazole, miconazole nitrate and any possible stereo isomers and derivatives thereof; piroctone olamine (Octopirox); ciclopirox olamine; anti-psoriasis agents such as vitamin D analogs, e.g. calcipotriol, calcitriol, and tacaleitrol; vitamin A analogs such as esters of vitamin A, e.g. vitamin A palmitate and vitamin A acetate, retinyl propionate, retinaldehyde, retinol, and retinoic acid; corticosteroids such as hydrocortisone, clobetasone, butyrate, clobetasol propionate menthol, pramoxine hydrochloride, and mixtures thereof.

Examples of benefit agents suitable for treating hair loss include, but are not limited to potassium channel openers or peripheral vasodilators such as minoxidil, diazoxide, and compounds such as N*-cyano-N-(tert-pentyl)-N'-3-pyridinyl-guanidine ("P-1075"); saw palmetto extract, vitamins, such as vitamin E and vitamin C, and derivatives thereof such as vitamin E acetate and vitamin C palmitate; hormones, such as erythropoietin, prostaglandins, such as prostaglandin E1 and prostaglandin F2-alpha; fatty acids, such as oleic acid; diruretics such as spironolactone; heat shock proteins ('HSP"), such as HSP 27 and HSP 72; calcium channel blockers, such as verapamil HCL, nifedipine, and diltiazemamiloride; immunosuppressant drugs, such as cyclosporin and Fk-506; 5 alpha-reductase inhibitors such as finasteride; growth factors such as, EGF, IGF and FGF; transforming growth factor beta; tumor necrosis factor; non-steroidal anti-inflammatory agents such as benoxaprofen; retinoids such as retinal and tretinoin; cytokines, such as IL-6, IL-1 alpha, and IL-1 beta; cell adhesion molecules such as ICAM; glucorcorticoids such as betametasone; botanical extracts such as aloe, clove, ginseng, rehmannia, swertia, sweet orange, zanthoxylum, Serenoa repens (saw palmetto), Hypoxis rooperi, stinging nettle, pumpkin seeds, and rye pollen; other botanical extracts including sandlewood, red beet root, *chrysanthemum*, rosemary, burdock root and other hair growth promoter activators; homeopathic agents such as Kalium Phosphoricum D2, Azadirachta indica D2, and Joborandi DI; genes for cytokines, growth factors, and male-pattered baldness; antifungals such as ketoconazole and elubiol; antibiotics such as streptomycin; proteins inhibitors such as cycloheximide; acetazolamide; benoxaprofen; cortisone; diltiazem; hexachlorobenzene; hydantoin; nifedipine; penicillamine; phenothaiazines; pinacidil; psoralens, verapamil; zidovudine; alpha-glucosylated rutin having at least one of the following rutins: quercetin, isoquercitrin, hespeddin, naringin, and methyl-hesperidin, and flavonoids and transglycosidated derivatives thereof; and mixtures thereof.

Examples of benefit agents suitable for use in inhibiting hair growth include: serine proteases such as trypsin; vitamins such as alpha-tocophenol (vitamin E) and derivatives thereof such as tocophenol acetate and tocophenol palmitate; antineoplastic agents, such as doxorubicin, cyclophosphamide, chlormethine, methotrexate, fluorouracil, vincristine, daunorubicin, bleomycin and hydroxycarbamide; anticoagulants, such as heparin, heparinoids, coumaerins, detran and indandiones; antithyroid drugs, such as iodine, thiouracils and carbimazole; lithium and lithium carbonate; interferons, such as interferon alpha, interferon alpha-2a and interferon alpha-2b; retinoids, such as retinol (vitamin A), isotretinoin: glucocorticoids such as betamethasone, and dexamethosone; antihyperlipidaemic drugs, such as triparanol and clofibrate; thallium; mercury; albendazole; allopurinol; amiodarone; amphetamines; androgens; bromocriptine; butyrophenones; carbamazepine; cholestyramine; cimetidine; clofibrate; danazol; desipramine; dixyrazine; ethambutol; etionamide; fluoxetine; gentamicin, gold salts; hydantoins; ibuprofen; impramine; immunoglobulins; indandiones; indomethacin; intraconazole; levadopa; maprotiline; methysergide; metoprolol; metyrapone; nadolol; nicotinic acid; potassium thiocyanate; propranolol; pyridostimine; salicylates; sulfasalazine; terfenadine; thiamphenicol; thiouracils; trimethadione; troparanol; valproic acid; and mixtures thereof.

Examples of suitable anti-aging agents include, but are not limited to inorganic sunscreens such as titanium dioxide and zinc oxide; organic sunscreens such as octyl-methoxy cinnamates and derivatives thereof; retinoids; copper containing peptides; vitamins such as vitamin E, vitamin A, vitamin C, vitamin B, and derivatives thereof such as vitamin E acetate, vitamin C palmitate, and the like; antioxidants including beta carotene, alpha hydroxy acids such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, glycolic acid, isopropyl pyruvate, methyl pyruvate, mucic acid, pyruvic acid, saccharic acid, saccaric acid 1,4-lactone, tartaric acid, and tartronic acid; beta hydroxy acids such as beta-hydroxybutyric acid, beta-phenyl-lactic acid, beta-phenylpyruvic acid; polyphenolics; botanical extracts such as green tea, soy products, milk thistle, algae, aloe, angelica, bitter orange, coffee, goldthread, grapefruit, hoellen, honeysuckle, Job's tears, lithospermum, mulberry, peony, puerarua, nice, safflower, and mixtures thereof.

Examples of suitable anti-acne agents include, but are not limited to topical retinoids (tretinoin, isotretinoin, motretinide, adapalene, tazarotene, azelaic acid, retinol); salicylic acid; benzoyl peroxide; resorcinol; antibiotics such as tetracycline and isomers thereof, erythromycin, and the anti-inflammatory agents such as ibuprofen, naproxen, hetprofen; botanical extracts such as *alnus, arnica, artemisia capillaris*, asiasarum root, birrh, *calendula*, chamomile, cnidium, comfrey, fennel, galla rhois, hawthorn, houttuynia, *hypericum*, jujube, kiwi, licorice, *magnolia*, olive, peppermint, philodendron, *salvia*, sasa albo-*marginata*; imidazoles such as ketoconazole and elubiol.

Examples of suitable depigmentation agents include, but are not limited to soy products, retinoids such as retinol; Kojic acid and its derivatives such as, for example, kojic dipalmitate; hydroquinone and it derivatives such as arbutin; transexamic acid; vitamins such as niacin, vitamin C and its derivatives; azelaic acid; placertia; licorice; extracts such as chamomile and green tea, and mixtures thereof, with retinoids, Kojic acid, soy products, and hydroquinone being particularly suitable examples.

Examples of suitable anti-hemorrhoidal products include, but are not limited to anesthetics such as benzocaine, pramoxine hydrochloride, and mixtures thereof; antiseptics such as benzethonium chloride; astringents such as zinc oxide, bismuth subgallate, balsam Peru, and mixtures thereof; skin protectants such as cod liver oil, vegetable oil, and mixtures thereof.

Examples of vasodilators include, but are not limited to minoxidil, diazoxide, and compounds such as N*-cyano-N-(tert-pentyl)-N'-3-pyridinyl-guanidine ("P-1075").

Examples of suitable shine-control agents include, but are not limited to hydrated silica, kaolin, and bentonite. Examples of suitable anti-histamines include, but are not limited to diphenhydramine HCl.

Examples of suitable antiinfectives include, but are not limited to benzalkonium chloride, hexamidine, and hydrogen peroxide. Examples of suitable wound healing promoters include, but are not limited to chitosan and its derivatives. Examples of suitable poison ivy and poison oak products include, but are not limited to bentonite, hydrocortisone, menthol, and lidocaine. Examples of burn products include, but are not limited to benzocaine and lidocaine. Examples of suitable anti-diaper rash products include but are not limited to zinc oxide and petrolatum. Examples of suitable prickly heat products include, but are not limited to zinc oxide. Examples of suitable sensates include, but are not limited to menthol, fragrances, and capsaicin.

Benefit agents that may be particularly suitable for use with the shaped film product 100 include, DMAE, soy products, colloidal oatmeal, sulfonated shale oil, olive leaf, elubiol, 6-(1-piperidinyl)-2,4-pyrimidinediamine-3-oxide, finasteride, ketoconazole, salicylic acid, zinc pyrithione, coal tar, benzoyl peroxide, selenium sulfide, hydrocortisone, sulfur, menthol, pramoxine hydrochloride, tricetylmonium chloride, polyquaternium 10, panthenol, panthenol triacetate, vitamin A and derivatives thereof, vitamin B and derivatives thereof, vitamin C and derivatives thereof, vitamin D and derivatives thereof, vitamin E and derivatives thereof, vitamin K and derivatives thereof, keratin, lysine, arginine, hydrolyzed wheat proteins, copper containing compounds such as copper containing peptides and copper salts, hydrolyzed silk proteins, octyl methoxycinnamate, oxybenzone, avobenzone, minoxidil, saw palmetto extract, titanium dioxide, zinc dioxide, retinol, erthromycin, tretinoin, and mixtures thereof.

Benefit agents that may be of particularly suitable for use the shaped film product 100 include neo-collagen promoters (e.g. retinoids such as retinal and copper-containing peptides), skin firming agents (e.g. DMAE), and depigmenting agents (e.g. soy).

The amount of the benefit agent that may be used may vary depending upon, for example, the ability of the benefit agent to penetrate through the skin or nail, the specific benefit agent chosen, the particular benefit desired, the sensitivity of the user to the benefit agent, the health condition, age, and skin and/or nail condition of the user, and the like. In sum, the benefit agent is used in a "safe and effective amount," which is an amount that is high enough to deliver a desired skin or nail benefit or to modify a certain condition to be treated, but is low enough to avoid serious side effects, at a reasonable risk to benefit ratio within the scope of sound medical judgment.

The benefit agent may be formulated, mixed, or compounded with other ingredients into a composition (e.g. liquid, emulsion, cream, and the like) wherein the other ingredients do not detract from the functionality of the benefit agent. A delivery agent that enhances the absorption of the one or more benefit agents into the skin may be formulated with the benefit agent to fulfill this function. Suitable delivery agents include, for example, sulfoxides, alcohols such as ethanol; fatty acids such as, for example, linoleic acid or oleic acid, fatty esters such as, for example, may be produced from reacting a C3-C10 carboxylic acid with a C10-C20 fatty alcohol; a polyol, an alkane, an amine, an amide, a turpene, a surfactant, a cyclodextrin or combinations thereof among other agents known to the art to be suitable for enhancing the penetration of various benefit agents through the stratum corneum into deeper layers of the skin.

The concentration of the benefit agent within the composition is variable. Unless otherwise expressed herein, typically the benefit agent is present in the composition in an amount, based upon the total weight of the composition/system, from about 0.01 percent to about 20 percent, such as from about 0.01 percent to about 5 percent (e.g., from about 0.01 percent to about 1 percent).

This composition that includes the benefit agent may also serve as a coupling composition as described previously and may include ingredients that enable the composition to possess one of these functions.

In addition to, or in place of one or more of the components described above, fragrances, flavors, sweeteners, coloring agents, pigments, dyes and the like may be added to the film-forming composition of the present invention.

The invention claimed is:

1. A process for forming a flexible, shaped adhesive film product comprising the steps of:
   a. placing an unscreened stencil mask having a delivery surface and an opposite substrate-facing surface, a thickness of greater than about 0.4 mm, and at least one aperture having a design corresponding to the desired shaped adhesive film product over a substrate having a releasable surface;
   b. delivering a liquid, film-forming composition at a flow rate through a nozzle in partial sealing engagement with the delivery surface of the stencil mask to the at least one aperture of the mask to form a raw shape on the substrate wherein the flow rate of the liquid, film-forming composition is controlled to correspond to a void volume defined by a projection of a delivery opening of the nozzle, substrate and stencil mask sidewalls; wherein the nozzle has machine direction dimension less than that of the stencil mask aperture;

c. removing the stencil mask;

d. solidifying the liquid, film-forming composition to provide the flexible, shaped adhesive film product disposed on the substrate and having a pressure-sensitive adhesive surface in contact with the substrate;

wherein the flexible, shaped adhesive film product is arranged and configured to be removable from the releasable surface of the substrate for use independent of the substrate.

2. The process of claim 1 wherein the stencil mask is disposed on the surface of a rotary drum having an interior, and the at least one aperture communicates with the interior of the rotary drum.

3. The process of claim 1 wherein the nozzle has cross direction dimension greater than that of the stencil mask aperture.

4. The process of claim 1 wherein the step of delivering a liquid, film-forming composition in a controlled manner through a nozzle comprises delivering the liquid, film-forming composition from a positive displacement pump.

5. A process for forming a multilayered, flexible, shaped adhesive film product comprising the steps of:

a. placing a first unscreened stencil mask having a delivery surface and an opposite substrate-facing surface, a thickness of greater than about 0.4 mm, and at least one aperture having a design corresponding to a desired shape of a portion of the shaped adhesive film product over a substrate having a releasable surface;

b. delivering a first liquid, film-forming composition through the at least one aperture of the first unscreened mask to form a first raw, unsolidified shape having a thickness on the substrate;

c. removing the first mask;

d. placing a second unscreened stencil mask having a thickness, a delivery surface and an opposite substrate-facing surface and at least one aperture having a design corresponding to the desired shape of a second portion of the shaped adhesive film product over the first raw; unsolidified shape, wherein the first raw shape is no larger than the at least one aperture of the second unscreened stencil mask and wherein the thickness of the second unscreened stencil mask is greater than the thickness of the first raw shape;

e. controlling delivery of a second liquid; film-forming composition to a void volume defined by:

i. a volume of a projection of a delivery opening of a nozzle, substrate and mask sidewalls, less the volume of the first raw, unsolidified shape corresponding to the projection of the delivery opening; and ii. delivering a controlled volume, equivalent to the void volume, of the second liquid, film-forming composition through the nozzle to the second unscreened stencil mask aperture; wherein the nozzle has a machine direction dimension less than that of the second unscreened stencil mask aperture;

f. removing the second unscreened stencil mask; and g. simultaneously solidifying the first and second raw shapes to provide the multilayered, flexible, shaped adhesive film product disposed on the substrate and having a pressure-sensitive adhesive surface in contact with the substrate;

wherein the multilayered, flexible, shaped adhesive film product is arranged and configured to be removable from the releasable surface of the substrate for use independent of the substrate.

6. The process of claim 5 wherein the second unscreened stencil mask is disposed on the surface of a rotary drum having an interior, and the at least one aperture communicates with the interior of the rotary drum.

7. The process of claim 5 wherein the nozzle has cross direction dimension greater than that of the second unscreened stencil mask aperture.

8. The process of claim 5 wherein the step of delivering the controlled volume of the second liquid, film-forming composition to the second unscreened stencil mask aperture comprises delivering the second liquid, film-forming composition from a positive displacement pump.

* * * * *